United States Patent [19]

Gutoff

[11] 4,275,587
[45] Jun. 30, 1981

[54] METHOD AND APPARATUS FOR DYNAMIC WETTING ANGLE MEASUREMENT

[75] Inventor: Edgar B. Gutoff, Brookline, Mass.

[73] Assignee: Polaroid Corporation, Cambridge, Mass.

[21] Appl. No.: 81,089

[22] Filed: Oct. 1, 1979

[51] Int. Cl.³ ............................................. G01N 13/02
[52] U.S. Cl. ...................................................... 73/64.4
[58] Field of Search ......................................... 73/64.4

[56] References Cited

FOREIGN PATENT DOCUMENTS 65-27192  7/1970  Japan ........................................ 73/64.4
489023  10/1975  U.S.S.R. ................................... 73/64.4

OTHER PUBLICATIONS

Fowkes, F. M., et al. *The State of Monolayers Adsorbed at the Interface Solid-Aqueus Solution*, 62 J.A.C.S., pp. 3377-3386, 1940.
Ablett, R. *An Investigation of the Angle of Contact between Paraffin Wax & Water*, 26 Philos. Mag., pp. 244-267, 1923.
Wilkinson, W. L., *Entrainment of Air by a Solid Surface Entering a Liquid/Air Interface*, Chem. Eng. Sci. vol. 30, pp. 1227-1230, 1975.
Inverarity, G. *Dynamic Wetting of Glass Fibre & Polymer Fibre*, Brit. Polymer Jour. vol. 1, pp. 245-251, Nov. 1969.
Kennedy, B. S., et al, *Dynamic Fluid Interface Displacement and Prediction of Air Entrainment*, Journ. of Coll. & Interface Sci. 62(1): pp. 48-62, Oct., 1977.
Dyba, R. V. et al, *Dynamic Measurements of the Wetting of Single Filaments*, Textile Res. Journ. 40(10): pp. 884-890, Oct., 1970.

*Primary Examiner*—Gerald Goldberg
*Assistant Examiner*—Joseph W. Roskos
*Attorney, Agent, or Firm*—John W. Ericson

[57] ABSTRACT

A method of measuring the dynamic wetting angle between a liquid and a solid surface moving into the liquid as a function of the speed of the solid surface relative to the liquid comprising the steps of moving the solid surface into the liquid at a constant speed, adjusting the angle of the surface entering the liquid until the wetting angle is equal to the angle between the solid surface and the quiescent surface of the surrounding liquid, and measuring said adjusted angle. In another embodiment, the speed of the solid surface entering at a selected angle is adjusted until the meniscus adjacent the surface becomes level, and the speed is measured.

8 Claims, 15 Drawing Figures

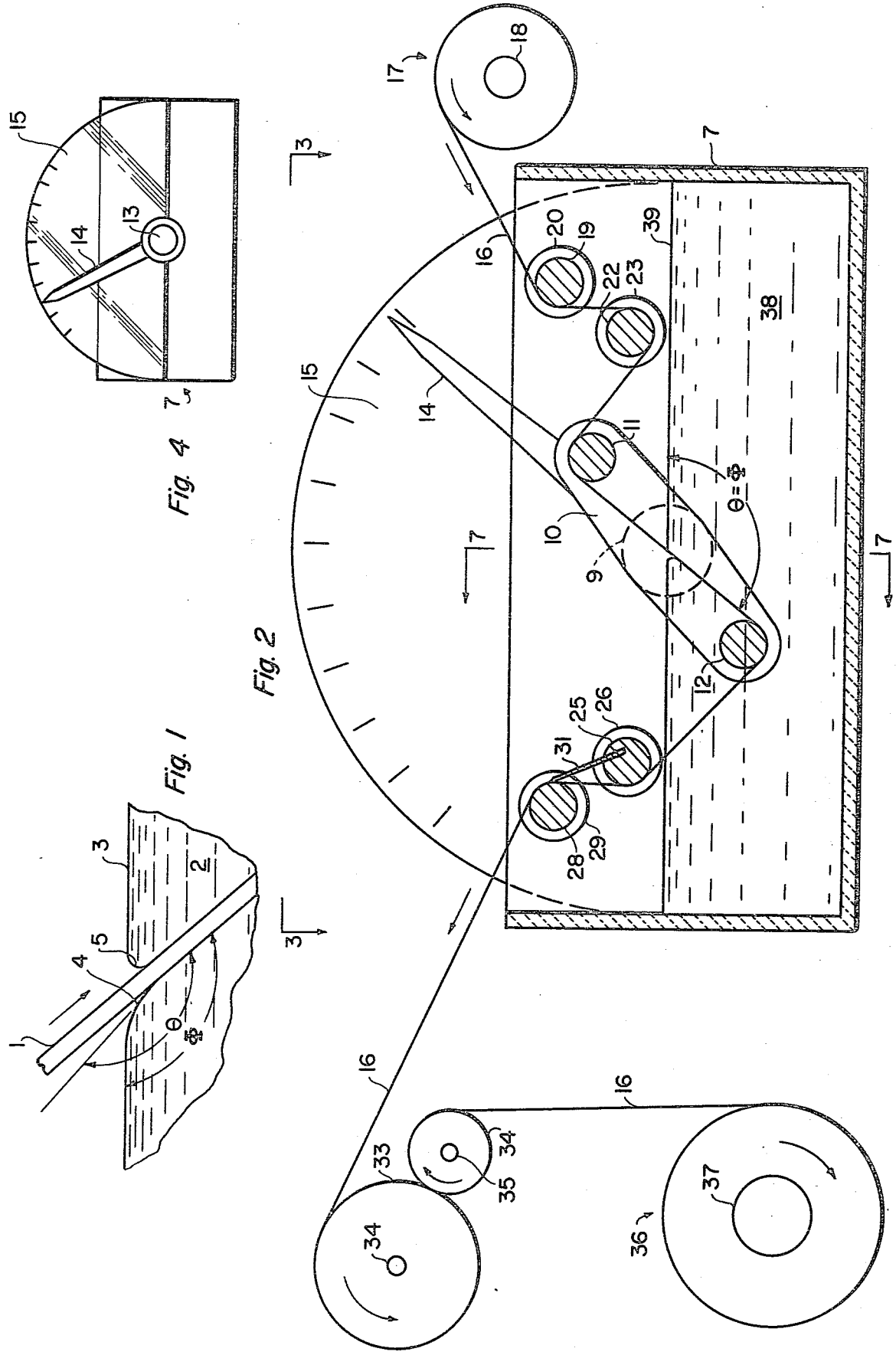

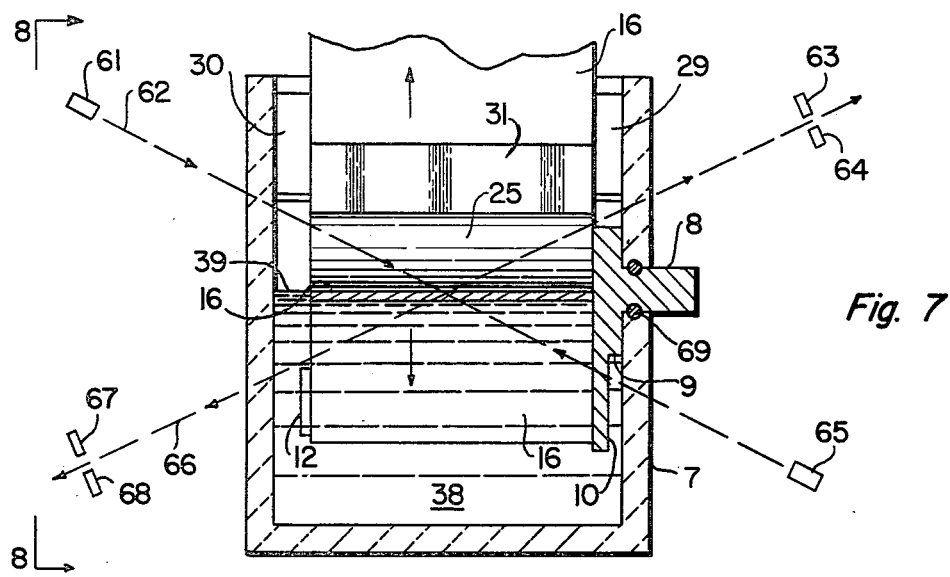
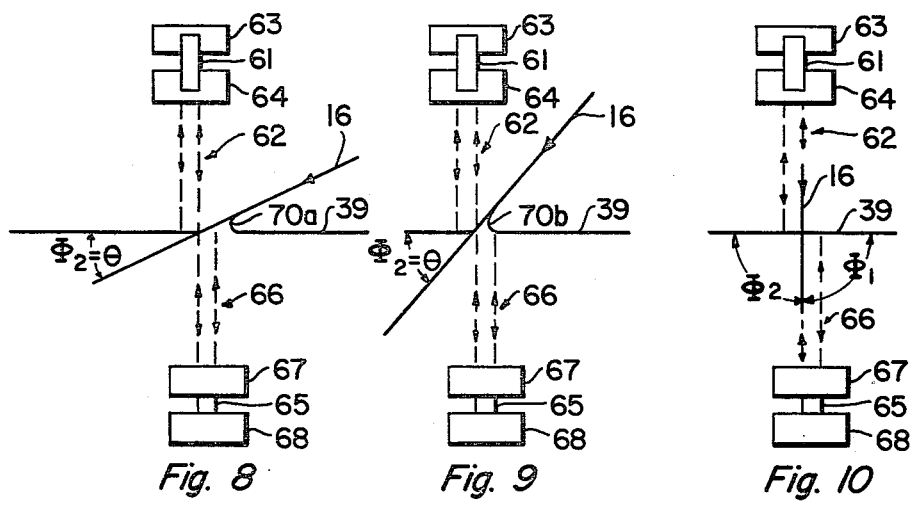
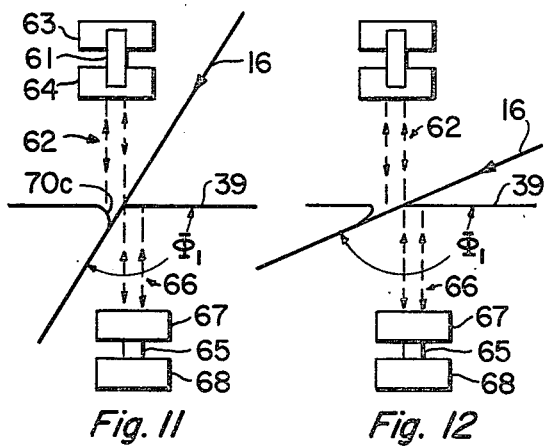
Fig. 7
Fig. 8　　Fig. 9　　Fig. 10
Fig. 11　　Fig. 12

METHOD AND APPARATUS FOR DYNAMIC WETTING ANGLE MEASUREMENT

This invention relates to the art of measuring and testing, and particularly to novel methods and apparatus for measuring the dynamic contact angle between a liquid and a solid surface moving into the liquid.

The dynamic angle of wetting between a liquid and a solid surface moving into the liquid is of interest in many fields of technology, particularly where coating, dipping or treating a solid with a liquid is involved. For any particular combination of liquid and solid, there is some speed at which the contact angle approaches 180°, whereupon gas at the liquid-solid interface becomes entrained and wetting becomes incomplete. This can considerably alter the process time for a system in which the contact time between liquid and solid is desired to be constant. As another example, in processes in which a liquid is coated on a solid surface, such as the surface of a web, the onset of air entrainment may give rise to unacceptably uneven coating. There has thus been considerable interest in determining how the dynamic contact angle is affected by various properties of the liquid and solid components that enter into the liquid-solid contact process. In order to address this question, various methods have been devised for measuring the dynamic contact angle between particular liquids and solid surfaces moving into the liquids.

The static contact angle between a solid surface and a liquid in which the solid surface is partially immersed is relatively easy to measure. One approach makes use of a plate having a surface of the kind to be investigated. The plate is partially immersed in the liquid, and tilted until the static contact angle is equal to the angle between the surface of the solid and the surface of the surrounding liquid.

This method, and apparatus for carrying it out, are described by F. M. Fowkes and W. D. Harkins in an article entitled *The State of Monolayers Absorbed at the Interface Solid—Aqueous Solution*, published in the Journal of the American Chemical Society, Volume 62, pages 3377-3386 (1940). The article describes the tilting plate method used to measure the static contact angle between solid surfaces of paraffin, graphite, stibnite and talc and various liquids. It has been found, however, that the static contact angle is not particularly well correlated with the dynamic contact angle.

Much of the work done on dynamic contact angle measurement has been carried out at very low speeds, for example, 4 millimeters per second or less. One such study is reported by R. Ablett in an article entitled An Investigation Of The Angle Of Contact Between Paraffin Wax And Water, printed in the Philosophy Magazine, Volume 26, pages 244-256 (1923). There, a wax coated drum was immersed in water until the interface was level as detected by the shape of the image formed by a narrow, parallel beam of light reflected from the water adjacent the interface. The author recommends reflecting the beam from beneath or above the surface, depending on whether the static contact angle is greater or less than 90°. The drum was rotated and then raised or lowered until the liquid solid interface was again level. The contact angle was then determined as a function of the depth of immersion and the diameter of the sphere of the drum.

A later worker using the rotating drum method was W. L. Wilkinson, who determined the speed at which a rotating steel cylinder dipping into a liquid began entraining air. This work is described in *Entrainment of Air by a Solid Surface Entering a Liquid/Air Interface*, appearing in Chemical Engineering Science, Volume 30, pages 1227-1230, printed in Great Britain in 1975.

Various studies have been made on filaments plunging vertically into a liquid at considerable higher speeds than those mentioned above. G. Inverarity, in *Dynamic Wetting of Glass Fibre and Polymer Fibre*, published in the British Polymer Journal, Volume 1, November 1969, pages 245-251,, describes observing the solid-liquid-gas interface with such a plunging filament with a microscope and recording the angle photographically. B. S. Kennedy and R. Burley, in *Dynamic Fluid Interface Displacement and Prediction of Air Entrainment*, published in the Journal of Colloid and Interface Science, Volume 62, No. 1, Oct. 15, 1977, give data on contact angles between surfaces, for example, of mylar polyester, plunging vertically into a liquid, determined by photographically recording the liquid solid interface. While photographic techniques make possible the measurement of angles over the range from 0°-180°, the method is somewhat tedious. And it is difficult to obtain precision in the angular measurement because the meniscus profile is continually changing in radius so that it is hard to draw the correct tangent to the meniscus.

An alternate method of studying the contact angle between a filament vertically plunging into a liquid and the liquid is described by R. V. Dyba and B. Miller in *Dynamic Measurements of the Wetting of Single Filaments*, published in Textile Research Journal, Volume 40, No. 10, Pages 884-890. There, the interface between filament and liquid was observed by a beam reflected from below the surface of the liquid and the speed of the filament was adjusted until the interface was level. There was thus determined the so-called rise canceling velocity at which the angle of contact is 90°. This method permits rather precise determination of the rise canceling velocity, but is not useful in obtaining data on the dependence of the contact angle on speed because it only gives one angle and one speed.

The object of this invention is to facilitate the determination of the dynamic contact angle between a solid entering a liquid and the liquid as a function of speed, without the need for photographic recording, over a wide range of speeds.

Briefly, the above and other objects of the invention are obtained by means of novel apparatus for moving an elongated solid, such as a web of plastic or the like, into and out of a bath of liquid at a controllable speed, and adjusting the angle of the surface of the solid entering the liquid about an axis normal to the direction of movement of the surface and in the plane of the liquid surface. In accordance with one specific process in accordance with the invention, the angle of entry is adjusted at a particular speed of entry until the interface between the liquid and the solid surface is level. In accordance with one embodiment of the invention, means are provided for direct visually indicating to the operator when this condition has been obtained, and the angle at which it takes place.

The manner in which the apparatus of the invention is constructed, and the process of the invention practiced, will best be understood in the light of the following detailed description, together with the accompanying drawings, of various illustrative embodiments of the invention.

In the drawings:

FIG. 1 is a fragmentary diagrammatic sketch, illustrating the region about the interface between a liquid and a solid web plunging into the liquid;

FIG. 2 is a diagrammatic and schematic elevational sketch, with parts shown in cross section, of apparatus for carrying out the invention, with portions seen essentially along the lines 2—2 in FIG. 3;

FIG. 4 is a schematic rear view of the apparatus of FIG. 3, taken essentially along the lines 4—4 in FIG. 3 but on a reduced scale;

FIG. 7 is a diagrammatic elevational sketch of a modification of the invention, with corresponding parts shown as seen essentially along the lines 7—7 in FIG. 2 and with parts shown in cross section;

FIGS. 8, 9, 10, 11 and 12 are diagrammatic sketches illustrating the relationship between a web plunging into a liquid and two sets of detectors forming a part of the apparatus of FIG. 6, with the portions shown being seen essentially along the lines 8—8 in FIG. 7 and portions omitted;

Figure 3:
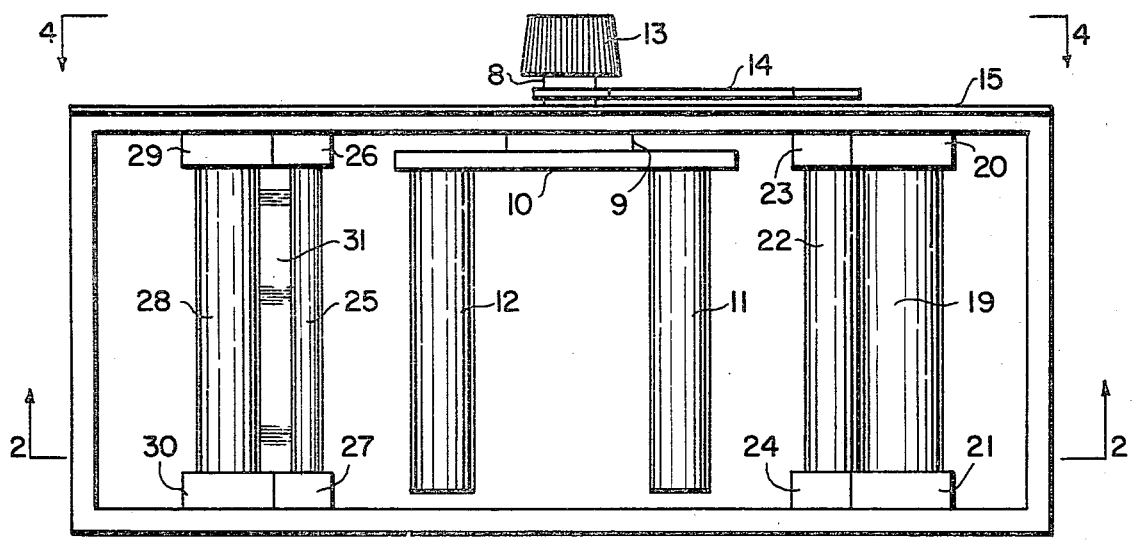
FIG. 3 is a plan view of a portion of the apparatus of FIG. 2 with the web removed, as seen essentially along the lines 3—3 in FIG. 2.

FIG. 1 shows a web 1 of solid material, such as paper, plastic, metal, or the like, plunging into a bath of liquid 2 at a sufficient speed so that the interface between liquid and solid on both sides is below the level of the surface 3 of the liquid 2 in the quiescent region removed from the meniscus. The dynamic contact angle between the liquid and the solid 1 is the same on the left side, where the meniscus is indicated at 4, as it is at the right side, where the meniscus is indicated at 5 when both surfaces of the solid are of the same material. The difference in the appearance of the menisci arises from the fact that the opposite surfaces of the web are at complementary angles to the surface of the liquid.

Confining attention to the meniscus 4, the angle theta is the contact angle between the liquid and the solid surface. The angle phi in FIG. 1 is the angle between the quiescent surface 3 of the liquid 2 and the solid 1. In the illustrated situation, the speed of the solid is sufficiently high so that the contact angle theta is nearing 180°, in which region gas entrainment into the solid-liquid interface would occur.

FIGS. 2, 3 and 4 show apparatus in accordance with the invention for measuring and indicating the dynamic contact angle of a moving web entering a liquid. As shown, the apparatus comprises a tank 7, preferably of transparent material such as glass, polymethylmethacrylate or the like, or, if of opaque material, provided with a suitable window for the observations to be described.

A shaft 8 passes through a suitable aperture formed in the side wall 6 of the tank 7 and is formed integral with an enlarged hub 9 that is in turn formed integral with an arm 10 to which are fixed a pair of guides 11 and 12. A knob 13 is secured to the shaft 8 to facilitate rotation of the shaft 8 by an operator. A suitable seal, such as an O-ring, now shown, may be provided between the shaft 8 and the wall 9 of the tank 7.

An indicating arm 14 is secured to the shaft 8 and cooperates with a protractor 15 secured to the wall 9 of the tank 7. The protractor 15 is also conveniently of transparent material. A web 16 of a material to be investigated is taken from a supply reel 17 having an arbor 18 mounted adjacent to the tank 7 for rotation in the sense indicated by the arrow. From the supply reel, the web 16 passes over a first fixed guide 19 having flanges 20 and 21 secured to the walls of the tank 7. The web 16 passes over the guide 19 and under a guide 22 having flanges 23 and 24 secured to the walls of the tank. The web 16 next passes over the guide 11, under the guide 12, and under and around a guide 25 having flanges 26 and 27 secured to the walls of the tank. The web passes from the guide 25 over a guide 28 having flanges 29 and 30 secured to the walls of the tank. A wiper blade 31 is secured in a notch in the spool 25 to remove liquid from the surface of the web 16.

As shown in FIG. 2, the web 16 passes out of the tank 7 and around an idler roll 33, having a surface of rubber or the like, and mounted on a shaft 34. The shaft 34 is mounted for rotation in the sense indicated by the arrow in convenient position adjacent to tank 7.

The web 16 is driven by a drive roll 34 engaging the web and holding it against the surface of the roller 33. The drive roller 34 is provided with a shaft 35. The shaft 35 is arranged to be driven at a constant speed that is adjustable over a desired range of investigation, by any conventional speed control means, not shown. The web speed may be detected in any conventional manner, or with an indicating tachometer driven by one of the shafts, such as the shaft 35. The drive roll 34 is preferably made of a material that will engage the web 16 with friction, such as rubber or the like.

The web 16 is taken up on a take-up roll 36 having an arbor 37 that is arranged to be driven through a slip clutch, not shown, with an input speed greater than the speed at which the web 16 is driven at the minimum radius of the web on the arbor 37, so that it will be taken from the drive roll 34 under tension. Alternatively, the take-up roll can be omitted and the web 16 allowed to fall into a suitable bin for disposal or reuse.

In the operation of the apparatus of FIGS. 2, 3 and 4, a liquid 38 whose contact angle is to be measured is charged into the tank 7 to a level just below the level of the web 16 under the guide 22. When the level is coincident with the axis of rotation of the shaft 8 there will be least disturbance of the liquid when the knob is turned. It is noted that the orientation of the needle 14 on the protractor 15 should be such that the indication of the needle will agree with the angle between the web 16 and the surface of the liquid 38; for example, when the web 16 enters the liquid 38 at 90°, the needle 14 should indicate 90° on the protractor 15.

Figure 5:
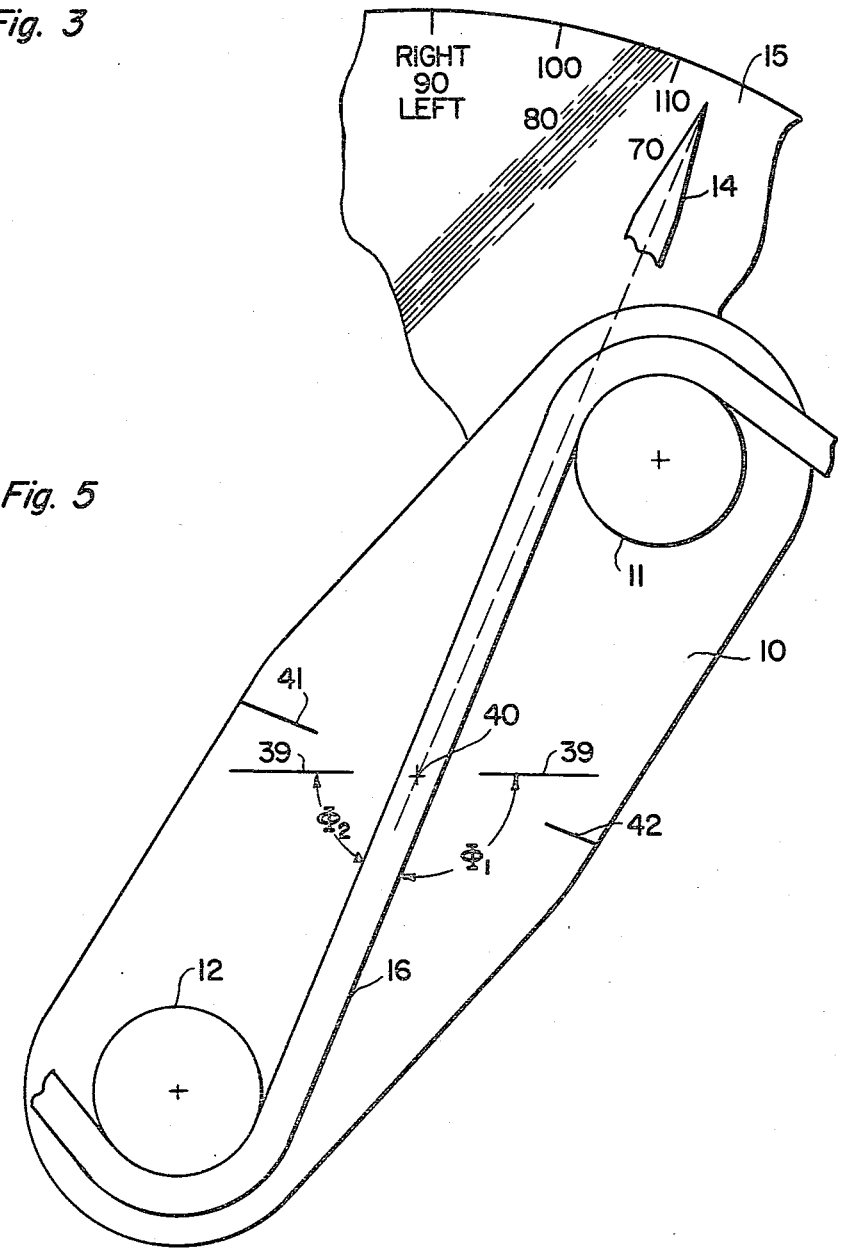
FIG. 5 is a diagrammatic fragmentary sketch of portions of the apparatus of FIGS. 2, 3 and 4, on an enlarged scale.

FIG. 5 illustrates certain relationships that are important in the practice of the invention. First, since the indicating needle 14, arm 10, and hub 9 of FIGS. 2–4 are all secured together, as indicated in FIG. 5 the center of rotation 40 of the arm 10 and the needle 14 will necessarily be the same, and will coincide with the axis of rotation of the shaft 8. If the guides 11 and 12 are of equal diameters and equally spaced from the center of rotation 40, with their centers lying on a common line through the center of rotation 40, the path of the web 16 between the guides 11 and 12 will necessarily intersect the center of rotation with the center 40 intersecting the central longitudinal axis of the web 16. The center of the protractor 15 should also coincide with the axis of rotation of the shaft 8. The needle 14 will then correctly indicate the angle between the web 16 and the surface 39 of the liquid 38. With this relationship, the meniscus on either side of the web 16 can be observed. However, when the angle $\Phi_1$ in FIG. 5, which corresponds to the meniscus at the right side of the web 16, is being observed, the angles indicated by the needle 14 on the protractor 15 should increase in a clockwise direction. On the other hand, if the left hand meniscus is observed and the angle $\Phi_2$ in FIG. 5 is to be determined, angles increasing in a counterclockwise direction should be indicated by the needle 14. This matter is facilitated by simply marking the protractor with a pair of arcuate angular scales, one increasing counterclockwise and the other increasing clockwise, as is conventionally done on protractors. These indicia can be supplemented by indicators on the two arcuate scales to indicate which meniscus is correlated with each scale, as suggested in FIG. 5. Since the liquid level 39 should preferably intersect the axis of rotation 40 of the web 16, it is convenient to place fiducial marks 41 and 42 on the arm 10 to assist in locating the liquid level correctly when the arm 10 is in some reference position, as for example at 90°.

The apparatus is adjusted by rotating the knob 13 with the web 16 moving at a desired speed until the meniscus on one side is level with the surface 39, indicating that the angle phi measured on the protractor 15 is equal to the angle theta that is the wetting angle between the liquid and the web 16. The speed of the web 16 can then be adjusted to a different value, and another observation taken until a desired amount of data has been collected.

Figure 6:
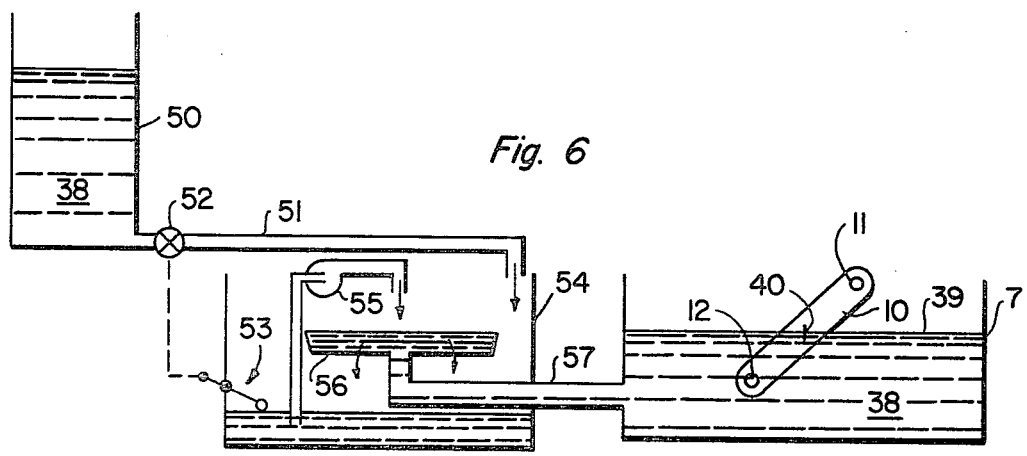
FIG. 6 is a diagrammatic sketch of apparatus useful in conjunction with the apparatus of FIGS. 1–3.

If the tank 7 is not large relative to the size of the web 16 and the duration of the observations that are to be made, it may be necessary to reestablish the level of the liquid 38 during the test so that it maintains the appropriate intersecting relationship with the center of rotation of the apparatus. FIG. 6 shows apparatus for maintaining the level of the liquid 38 constant despite depletion of liquid occuring by reason of liquid which wets the web 16 and is not completely removed by the wiper 31 in FIG. 2. As shown, the liquid 38 is contained in a supply tank 50. The tank 50 is connected to a pipe 51 through a valve 52 controlled by a conventional level control indicated at 53. Liquid is supplied through the pipe 51 to a secondary reservoir 54, whence it is pumped by a pump 55 into a spillover pan 56 having a level at the desired level 39 of the liquid in the tank 7. The spillover pan 56 is connected to the tank 7 by a conduit 57. It will be apparent that by means of this apparatus, the liquid level 39 will be maintained at a desired constant level.

FIG. 7 illustrates apparatus in accordance with the invention modified to permit automatic data recording. Parts corresponding to those shown in FIGS. 2-5 have been given corresponding reference characters. The web handling system for the web 16 may be the same as that described above. An O-ring seal 69 is shown provided between the shaft 8 and the wall of the tank 7 through which the shaft passes. The needle 14, knob 13, and protractor 15 are shown removed to facilitate automatic control of the shaft 8 in a manner to be described below in connection with FIG. 13. Alternatively, these parts can be retained if both manual and automatic operation are desired.

A first transducer set is arranged to produce a signal corresponding to the shape of the meniscus on the upper side of the intersection with the web 16. The upper scanning system comprises a light source 61 adapted to direct a beam of light, preferably a collimated horizontally oriented slit indicated by the dashed line 62, toward the surface of the liquid 38 in the vicinity of the meniscus with the web 16.

The beam 62 is reflected from the surface 39 up toward a pair of photodetectors 63 and 64 spaced by a gap through which the beam will pass if the liquid surface is level. If the meniscus is above the surface, the light will be reflected upwardly onto the photodetector 63. Conversely, if the meniscus is below the surface, the light will fall on the photodetector 64.

The differential in signal between the photodetectors 63 and 64 may be used to control the angle at which the web 16 enters the liquid 38 so that the angle can be changed until the meniscus is flat. More light falling on the photodetector 63 indicates that the angle should be decreased to approach this condition, whereas more light on the photodetector 64 indicates that the angle should be increased.

Referring to FIG. 2, it will be seen that the left hand meniscus could be illuminated by a light beam from above only if the angle between the left side of the web 16 and the surface 39 was below 90°, or perhaps slightly beyond 90°. Accordingly, referring to FIGS. 2 and 7, apparatus is also provided for looking at the meniscus on the right hand side of the web 16 as seen in FIG. 2 from below. This apparatus comprises a light source 65, which may be of the same type as the light source 61, producing a scanning beam 66 that passes between a pair of photodetectors 67 and 68 when the meniscus illuminated by the beam 66 is flat.

When the meniscus goes above the surface 39, light will be reflected onto the photodetector 67. On the other hand, when the meniscus goes below the surface, the light will be reflected onto the photodetector 68. When the photodetector 67 is illuminated more than the detector 68, it indicates that the angle of the web 16 should be decreased to approach the flat condition. When the photodetector 68 is more illuminated, this indicates that the angle of entry of the web 16 should be increased to approach the flat condition. A point to note in this regard is that the angle of the web 16 between its right side and the surface 39 is increased by a clockwise rotation of the arm 10 as seen in FIG. 2. Rotation in this same direction causes a decrease in the angle between the left side of the web and the surface 39. The application of these facts to the control of the shaft 8 will be explained below.

FIGS. 8 through 12 illustrate various conditions under which either the pair of sensors 63 and 64, or the pair 67 and 68, are used to detect the condition of equality between the contact angle of the liquid on the web 16, and the angle between the selected surface of the web 16 and the level 39 of the fluid in a region remote from the meniscus.

FIG. 8 illustrates the situation in which the web 16 is moving relatively slowly into the liquid at an angle $\Phi_2$ that equals the contact angle $\theta$, which condition is indicated by equal signals from the sensors 63 and 64 with the light beam 62 passing between them. The meniscus 70a on the right side of the web 16 is well above the surface, and under these conditions the signals from the sensors 67 and 68 would not be utilized.

FIG. 9 illustrates the situation when the web is moving at a higher speed than in FIG. 8, requiring an increased angle $\Phi_2$ for the meniscus on the left side of the web 16 to be flat. The meniscus 70b is still above the surface 39.

At a still higher speed, as illustrated in FIG. 10, the angles $\Phi_2$ and $\Phi_1$ would be equal, and equal to 90°, with the web 16 at the so-called rise-cancelling velocity of entry into the liquid. Either the signals from the detector 63 and 64, or the signals from the detectors 65 and 68, could be used to detect this condition.

As the speed of the web 16 continues to increase, as shown in FIG. 11, the meniscus 70c at the left side of the web 16 will go below the surface, and at the proper angle $\Phi_1$, the meniscus on the right side will be flat. This condition is now detected by the sensors 67 and 68, and the signals from the detector 63 and 64 are not utilized.

As shown in FIG. 12, as the speed continues to increase, the angle $\Phi_1$ will approach 180° before it equals the contact angle $\theta$. While in principle angles between nearly zero and almost 180° can be measured and detected with the appropriate use of the sensors 63 and 64 or 67 and 68, in practice using the manually controlled apparatus of the type shown in FIGS. 2–5, it was found that the most precise results were obtained at contact angles between 45° and 135°.

Figure 13:
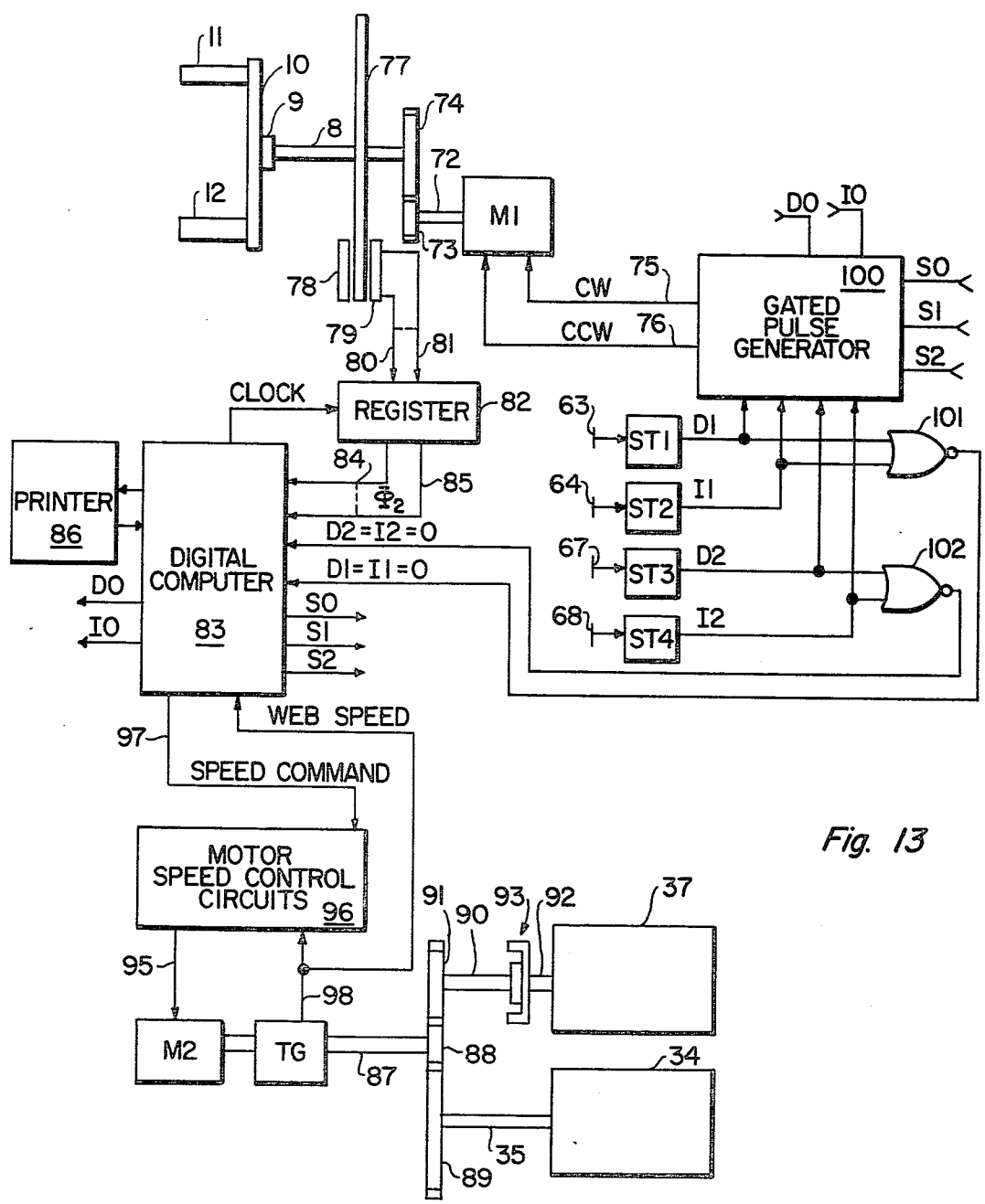
FIG. 13 is a diagrammatic block and wiring diagram of a control system for operating apparatus in accordance with the invention, particularly in accordance with the embodiment of FIG. 7, for automatic data recording.

FIG. 13 shows a control system usable with the apparatus of FIG. 7 to automatically record correlated values of web speed and contact angle. In FIG. 13, circuits are indicated by single leads, it being understood that return leads would be provided in a conventional manner, not shown.

Referring to FIG. 13, a motor M1 has a shaft 72 that is arranged to drive the shaft 8 through reduction gearing shown schematically as comprising a gear 73 fixed to the shaft 72 and a gear 74 fixed to the shaft 8. The motor M1 may be a conventional digital stepping motor of the type arranged to drive the shaft 72 in one direction in response to pulses applied over a lead 75, and in the opposite direction in response to pulses applied over a lead 76. Pulses CW applied over the lead 75 will cause the motor to run in such a direction that the shaft 8 will be moved clockwise, as seen from the left in FIG. 6 or as seen in FIG. 2. Similarly, pulses CCW applied over a lead 76 will cause the motor M1 to drive the shaft 8 counterclockwise.

The reduction ratio symbolized by the gears 73 and 74 may actually be considerably higher than would be practical with a simple pair of gears, so that the increment of motion of the shaft 8 corresponding to a single pulse such as CW or CCW will be very small. This relationship is desirable in order to allow the shaft 8 to be turned smoothly without jerking the web 16.

An optically coded disc 77 is fixed on the shaft 8. The disc 77 cooperates with a bank of light generating elements 78, such as light emitting diodes or the like, on one side of the disc, and a bank of photodetectors, which may be a charge coupled array, on the other side of the disc. Signals produced by this arrangement are supplied over any desired number of leads such as 80 and 81 to a register 82 into which they are copied at clock times indicated by a digital computer 83. The contents of the register 82 are made available to the computer 83 over leads such as 84 and 85, and may be copied into memory by the computer 83 at times determined by the computer and based on considerations to be described. The computer 83 may be any conventional general purpose digital computer programed to carry out the operations to be described, and is preferably associated with a printer 86, such as a conventional high speed line printer or the like, to enable recorded data to be printed out at convenient times.

The apparatus further comprises a speed control system for the drive roll 34 and for the take-up arbor 37 of the apparatus of FIG. 2. A conventional electric motor M2 has an output shaft 87 that drives a tachometer generator TG, and also drives a gear 88 fixed to the shaft 87. The gear 88 in turn drives the shaft 35 through a gear 89 fixed to the shaft 35, and drives a shaft 90 through a gear 91 fixed to the shaft 90. The gear ratios are preferably so chosen that the shaft 90 rotates faster than the shaft 35. The shaft 90 drives a shaft 92 through a slip clutch schematically shown at 93. This arrangement is for the purposes described above in connection with FIG. 2, so that the web 16 taken up on the arbor 37 will always be under tension.

The speed of the motor M2 is controlled by current supplied over a lead 95 from conventional motor speed control circuits 96. The motor speed control circuits 96 respond to a speed command signal supplied over a lead 97 under the control of the digital computer 83, and to speed signals supplied over a lead 98 from the tachometer generator TG both to the motor speed control circuits 96 and to the digital computer 83. For this purpose, a tachometer generator TG may be selected that will produce pulses at a repetition rate proportional to the speed of the web 16. Such pulses may be gated by the computer into a counter for a predetermined interval, and the count at the end of the interval copied into a register at times to be described. The speed command signal supplied by the computer may comprise a pulse train at a repetition rate corresponding to the desired speed.

The system shown in FIG. 13 operates in three sequential modes as directed by signals S0, S1, and S2 produced by the digital computer 83 in a manner to be described.

From the above description with reference to FIGS. 8–12, it will be apparent that the angle at which the meniscus at either the left or right side of the web 16 is flat at a given speed can be determined over the full range of 180° even though the actual angular range of movement of the web 16 need only be from 0°–90°. Advantage can be taken of this fact if so desired by driving the optically coded disc 77 from the shaft 8 through a 4 to 1 reduction ratio, such that a quarter of a revolution of the shaft 8, which is all that will be required, will correspond to a full revolution of the disc 77 and thus allow finer angular resolution.

The computer 83 may be programed to produce a first signal S0 to direct the shaft 8 to an initial position which may, for example, correspond to a small value of the angle $\Phi_2$, which is that angle that is represented by the contents of the register 82. For this purpose, in the operating mode in which signal S0 is present, the computer 83 may compare the contents of the register 82 with a programed starting angle $\Phi S$. When the angle $\Phi_2$ in the register 82 is less than $\Phi S$, the computer will produce a signal labeled I0. When the signal $\Phi_2$ is greater than $\Phi S$, the computer 83 will produce a level labeled D0 in FIG. 13.

The signals D0, I0, and S0, which may be digital binary signals, are applied to a gated pulse generator 100. The gated pulse generator 100 may comprise a pulse generator, such as an oscillator, or the like, together with gate circuits for gating pulses produced by the pulse generator, either onto the line 75 as pulses CW, or onto the line 76 at at pulses CCW. When the signals I0 and S0 are present, the gated pulses CW are produced. When the levels D0 and S0 are present, pulses CCW will be produced. In this manner, the shaft 8 will be initially positioned at an angle $\Phi_2$ equal to $\Phi S$.

The condition $\Phi_2$ equals $\Phi S$ may be taken by the computer as a signal to remove the level S0 and produce the signal S1. At the same time that the level S1 is produced, a first speed command signal is transmitted by the computer to the motor speed control circuits 96, causing the speed of the web to be brought to that command value. At the same time, the angle of the shaft 8 is controlled by the photodetectors 63 and 64.

As shown in FIG. 13, the photodetectors 63 and 64 are connected to Schmitt trigger circuits ST1 and ST2 such that when the photocell 63 is illuminated, a signal D1 will be produced, and when the photodetector 64 is illuminated a signal I1 will be produced. These signals are applied to the gated pulse generator 100 together with the level S1. In response to the signals D1 and S1, pulses CW are gated on to the line 75. In response to the signals I1 and S1, pulses CCW are gated on to the line 76. These pulses will cause the motor M1 to bring the shaft 8 to an angle such that the observed meniscus is flat and neither of the signals D1 nor I1 will be produced.

The signals D1 and I1 are applied to a conventional NOR gate 101 that will produce an output signal at logic 1 indicating $D1=I1=0$ when neither of the levels D1 and I1 is present. In response to this signal, the computer 83 may be programmed to copy the current web speed and the contents of the register 82 into associated memory domains in the computer. A new speed command signal can now be applied by the computer to the motor speed control circuits 96 over the lead 97, resulting in an increased speed of the web 16 that will cause a new angle to be determined in the manner just described.

The program can continue in the manner just described as additional web speeds represented by new speed command signals on the lead 97 are produced, until at some commanded web speed, the register 82 indicates that the shaft 8 is at 90°. During the S1 mode, the computer should be programed to compare the contents of the register 82 with binary signals representing 90°, and when the indication is that $\Phi_2$ equals 90°, the signals S1 will be removed and a level S2 will be produced.

With the signal S2 present, the photodetectors 67 and 68 will control the angle of the web. For this purpose, the photodetectors 67 and 68 are connected to Schmitt trigger circuits ST3 and ST4 respectively. The Schmitt trigger ST3 will produce a signal D2 when the photocell 67 is illuminated, and the Schmitt trigger ST4 will produce a signal I2 when the photodetector 68 is illuminated. These signals are applied to the gated pulse generator 100 together with the signal S2.

With signals S2 present and D2 present, pulses CCW will be gated onto the line 76. With signals I2 and S2 present, the pulses CW will be gated onto the line 75. In this manner, the angle of the shaft will be adjusted until both the signals D2 and I2 are absent.

The signals D2 and I2 are applied to a NOR gate 102 to produce a signal labeled $D2=I2=0$ at logic 1 when both D2 and I2 are absent. Upon receipt of this signal, the computer 83 will store the current web speed and the contents of the register 82 will be substracted from 180° and stored in correlated storage locations. Subtraction of 180° takes into account the fact that $\Phi_1$ and not $\Phi_2$ is now of interest, since $\Phi_1 = 180° - \Phi_2$.

A new speed command at a still higher speed can next be generated by the computer 83, and the process described above may be repeated until the highest speed command signal programed had been transmitted and the appropriate angle of the web 16 determined and registered.

The invention has thus far been described as involving setting the speed of the web and then adjusting the angle of entry until a flat meniscus is detected. However, the invention can also be practiced by fixing the angle of entry, then adjusting the web speed until a flat meniscus is observed, or automatically detected, and measuring or registering the speed at which the flat meniscus is obtained.

Figure 14:
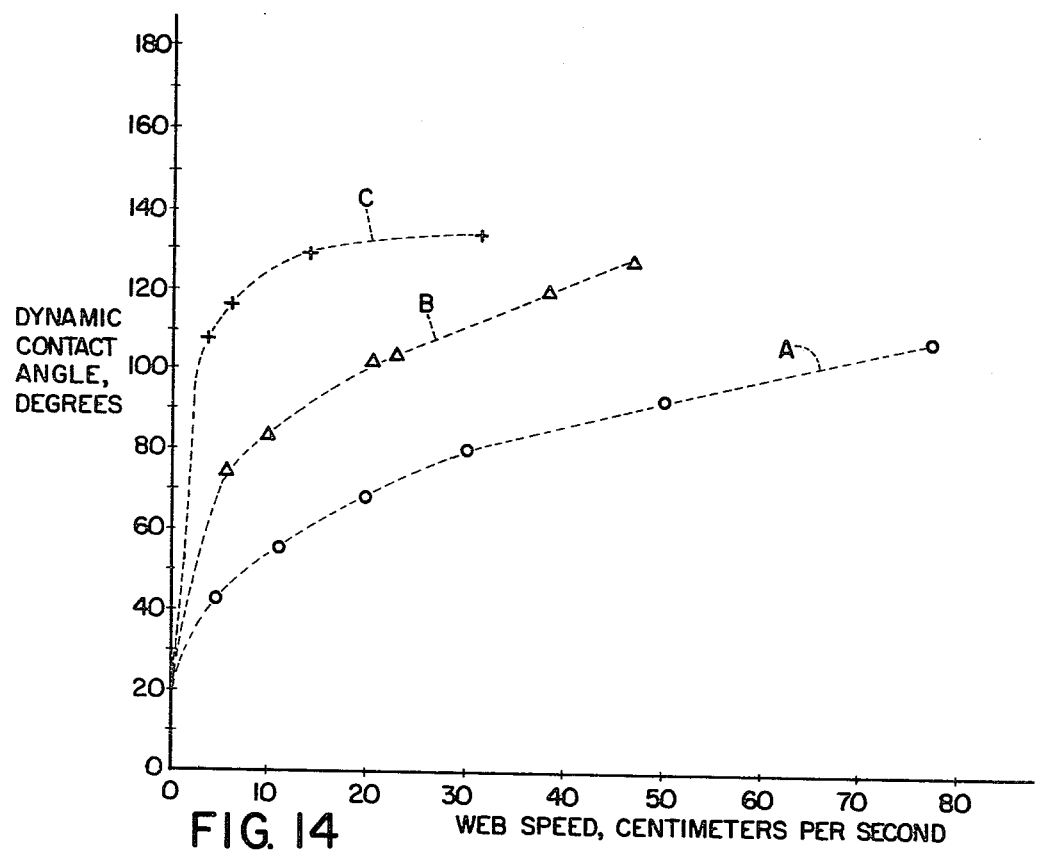
FIG. 14 is a graph of dynamic contact angle versus web speed showing data for three solutions.

FIG. 14 shows data taken on three solutions with apparatus in accordance with FIGS. 2-5. In FIG. 14, the circle, triangles and crosses represent data on water, a 2.7 weight percent solution of poly(vinyl alcohol) in water, and a 70 weight percent solution of glycerine in water, respectively. The solid was a 16 mm web of polyester coated with gelatin. The dashed curves A, B and C indicate correlations suggested by the data. The contact angles shown at zero web speed are static contact angles.

Figure 15:
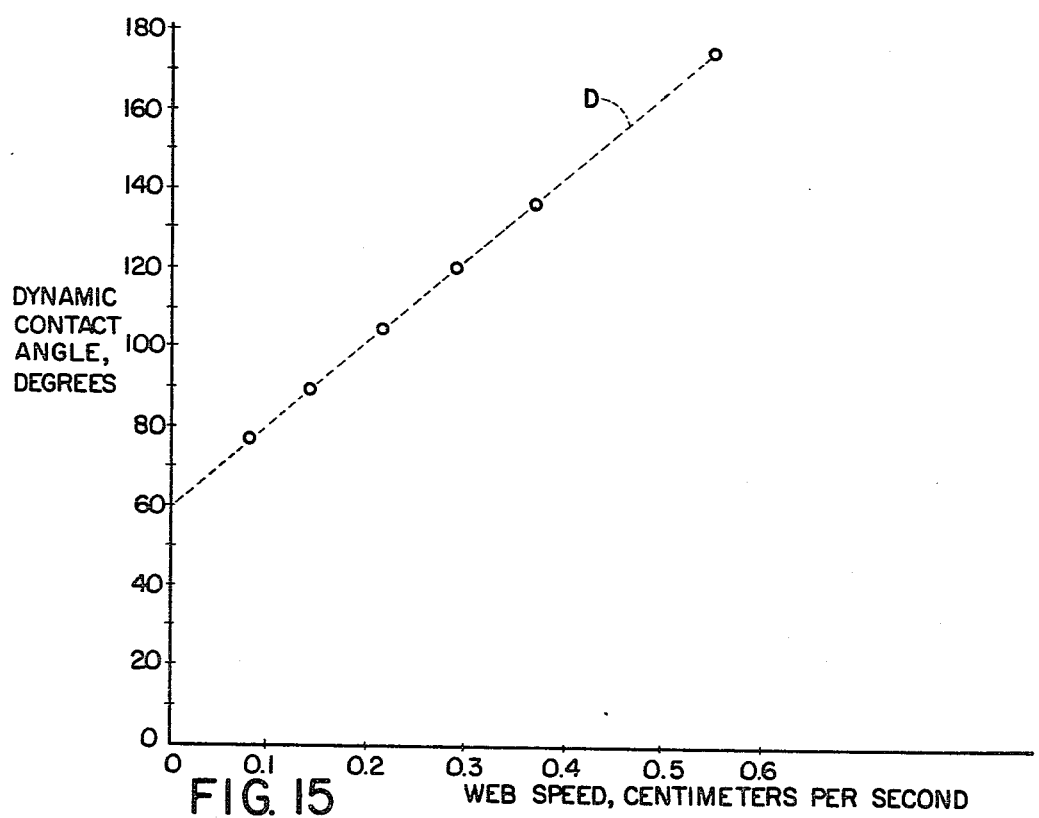
FIG. 15 is a graph of dynamic contact angle versus web speed showing data taken at a liquid-liquid-solid interface.

Apparatus in accordance with the invention is useful over a wide range of web speeds, and can also be used to measure contact angles at a liquid-liquid-solid interface. FIG. 15 shows data taken on a 16 mm web of polyester coated with gelatin plunging into a pool of water with a layer of kerosene 1 cm thick on the surface of the water. The contact angles shown are at the web-water-kerosene interface. It will be seen that the contact angle increases much more rapidly with speed than at an air-water-gelatin interface, as for curve A in FIG. 14.

In order to make measurements of web speed at a dynamic contact angle of 180°, as for the corresponding data point in FIG. 15, the apparatus was adjusted so that the web entered the liquid at 90°, and the speed then adjusted until entrainment of the fluid over the fluid whose contact angle was being measured began.

While the invention has been described with respect to the details of various illustrative embodiments, many changes and variations will occur to those skilled in the art upon reading this description. Such can obviously be made without departing from the scope of the invention.

Having thus described the invention, I claim:

1. The method of measuring the dynamic contact angle between a liquid and a solid surface moving into the liquid, comprising the steps of moving said surface into the liquid at a constant speed, adjusting the angle at which said surface enters the liquid by rotation of said surface about a fixed axis until the dynamic contact angle is equal to the angle between said surface and the quiescent surface of the liquid remote from the meniscus, and detecting said adjusted angle.

2. Apparatus for measuring the dynamic contact angle between a liquid and a moving web entering the liquid, comprising means for moving the web into and out of the liquid at a fixed speed, means for rotating the web about a fixed axis through and perpendicular to the central longitudinal axis of the web, and means for indicating the angle of the web relative to the surface.

3. The method of measuring the dynamic contact angle between a liquid and a solid surface moving into the liquid as a function of speed, comprising the steps of moving said surface into the liquid, adjusting the speed and angle of entry of said surface relative to the liquid over a range sufficient to find a plurality of corresponding speeds and contact angles at which the meniscus of the liquid adjacent the surface is level, and recording said corresponding speeds and contact angles.

4. The method of claim 3, in which each of said plurality of corresponding speeds and contact angles is found by setting the speed of said solid surface to a different one of a set of speeds in said range, and adjusting the angle of entry of the surface into the liquid until the meniscus adjacent said surface is level.

5. The method of claim 3, in which each of said plurality of corresponding speeds and contact angles is found by setting the angle of entry of said solid surface into the liquid to a different one of a set of angles in said range, and adjusting the speed of said solid surface until the meniscus adjacent said surface is level.

6. The method of claim 3, in which said solid surface is moved into the liquid through a gas.

7. The method of claim 3, in which said solid surface is moved into the liquid through another liquid.

8. Apparatus for measuring the dynamic contact angle between a liquid and a moving web entering the liquid, comprising a tank adapted to contain a quantity of liquid, guide means mounted on said tank for guiding a web into and out of said tank, a shaft, means mounting said shaft for rotation in said tank about a predetermined horizontal axis in the plane of the surface of a liquid in said tank at the level of said axis, an arm centrally mounted on a first end of said shaft in said tank and extending radially outward therefrom in opposite directions, means forming a pair of cylindrical web guides of equal radius in spaced relation on said arm, equidistant from said axis, and extending transversely from said arm, said shaft having an end extending outside of said tank, an indicating arm mounted on said shaft and extending radially outward thereof, and a protractor mounted on said tank and centered on said axis, said protractor comprising angular indicia adapted to cooperate with said indicating arm, whereby a web passing into and out of said tank and over one of said cylindrical web guides and under the other will rotate about said axis when said shaft is rotated through angles indicated by the position of said arm relative to said indicia.

* * * * *